United States Patent [19]

Ingber et al.

[11] Patent Number: 5,662,476
[45] Date of Patent: Sep. 2, 1997

[54] PROSTHETIC IMPLANT RESTORATION METHOD

[75] Inventors: Abraham Ingber, Potomac; Vincent Joseph Prestipino, North Bethesda, both of Md.

[73] Assignee: Nobel Biocare AB, Gothenburg, Sweden

[21] Appl. No.: 488,280

[22] Filed: Jun. 7, 1995

Related U.S. Application Data

[63] Continuation-in-part of Ser. No. 377,502, Jan. 24, 1995, Pat. No. 5,571,016, which is a continuation of Ser. No. 908,580, Jun. 29, 1992, abandoned.

[51] Int. Cl.$^6$ .................................................. A61C 11/00
[52] U.S. Cl. ........................................ 433/213; 433/173
[58] Field of Search ................................ 433/172, 173, 433/174, 175, 176, 213, 214

[56] References Cited

U.S. PATENT DOCUMENTS

| | | | |
|---|---|---|---|
| 4,955,811 | 9/1990 | Lazzara et al. | 433/173 |
| 5,035,619 | 7/1991 | Daftary | 433/173 |
| 5,052,929 | 10/1991 | Seal | 433/173 |
| 5,213,502 | 5/1993 | Daftary | 433/173 |
| 5,338,196 | 8/1994 | Beaty et al. | 433/172 |
| 5,492,471 | 2/1996 | Singer | 433/172 |

OTHER PUBLICATIONS

The Bio–Esthetic Abutment System™, Dafrary et al., Steri–Oss, Fall 1995.

*Primary Examiner*—Cary E. O'Connor
*Attorney, Agent, or Firm*—Law Offices Pollock, Vande Sande & Priddy

[57] ABSTRACT

A healing abutment embedded in edentulous bone remains in its implantation site in contouring contact with gingival tissue and has an impression coping mounted directly thereon for data transfer of the healing abutment position and shape to a replica of the implantation site on which a restorative prosthesis is formed. The prosthesis is transferred to the actual implantation site after removal of the healing abutment therefore when the gingival tissue has healed.

8 Claims, 9 Drawing Sheets

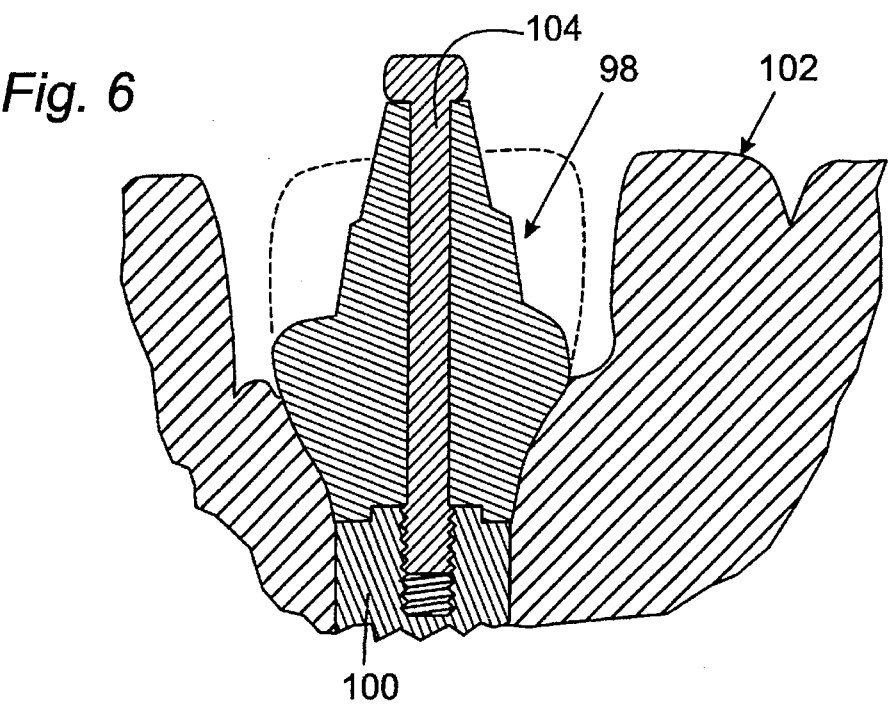
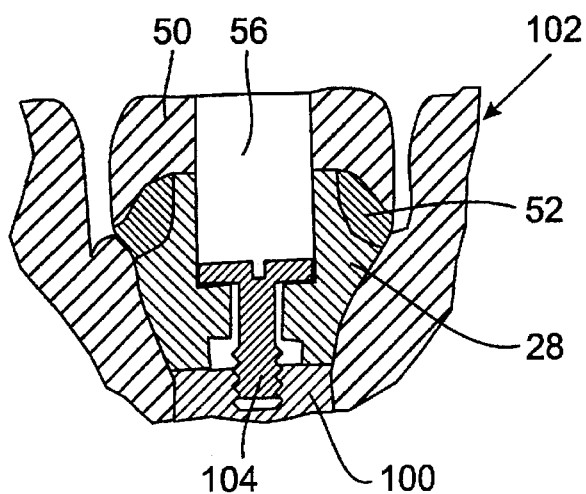
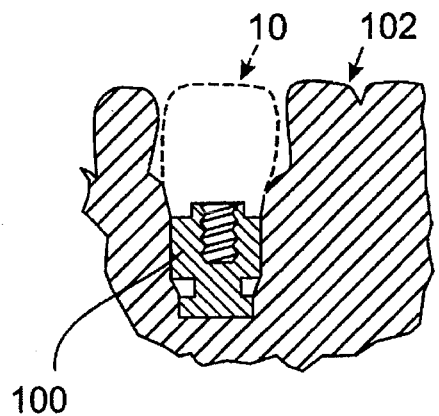

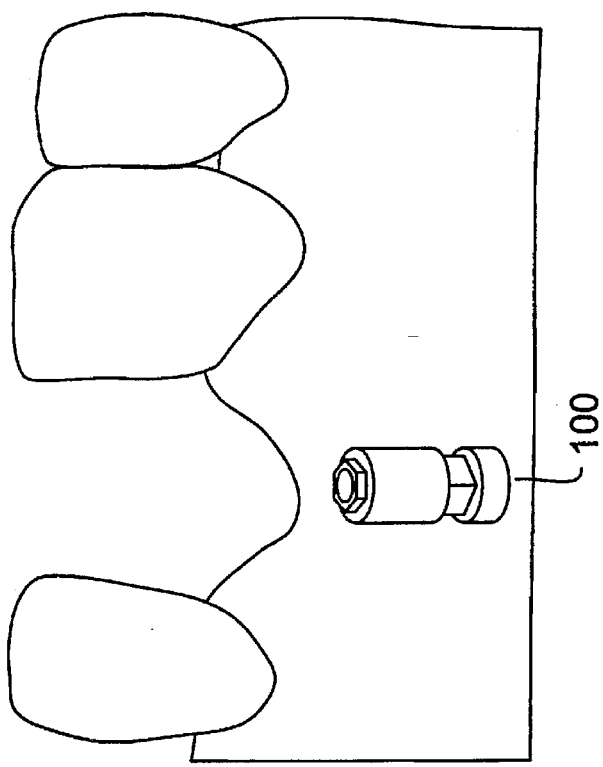
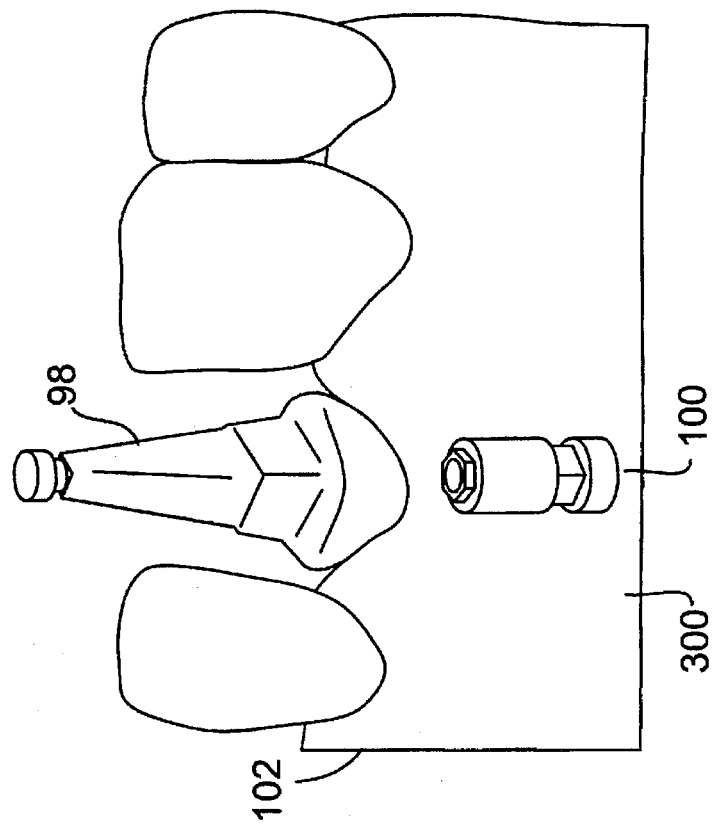

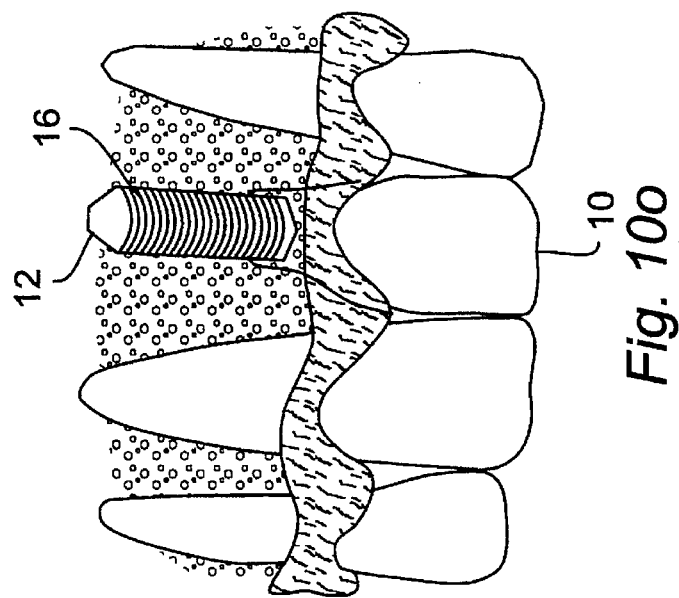
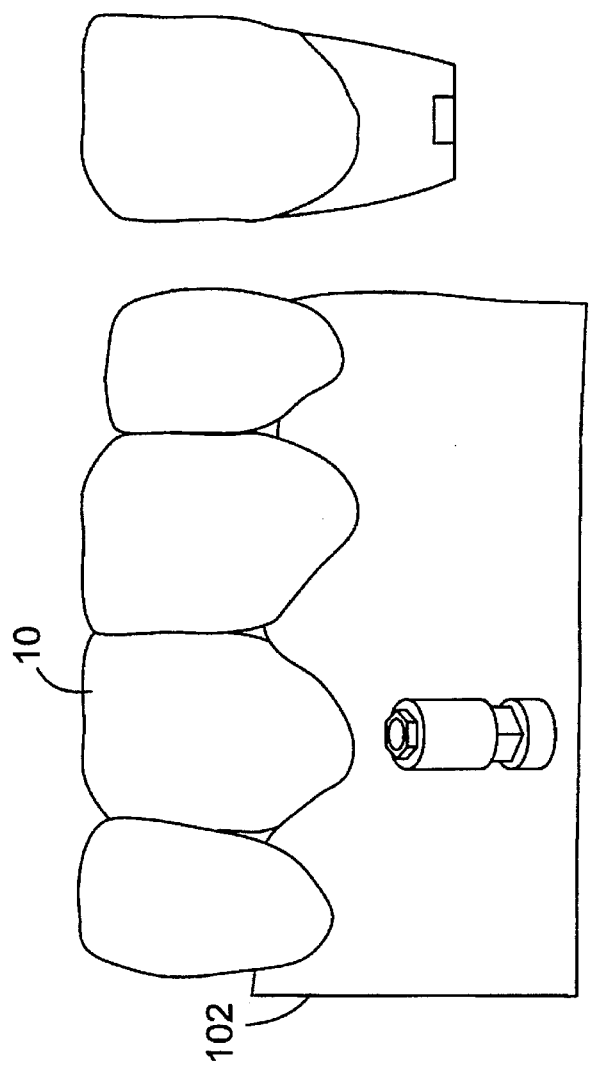
Fig. 10o
Fig. 10n
Fig. 10m 5,662,476

PROSTHETIC IMPLANT RESTORATION METHOD

The present invention relates in general to an improved method of installing a restorative tooth prosthesis, such as the dental implant disclosed in U.S. Pat. No. 5,125,839 to Ingber et al., with respect to which the present application is a continuation-in-part through a application, Ser. No. 08/377,502 filed Jan. 24, 1995 now U.S. Pat. No. 5,571,016, which is a continuation of 07/908,580 filed Jun. 29, 1992 now abandoned.

BACKGROUND OF THE INVENTION

Surgical procedures for extraction of a tooth in the edentulous bone of a patient's mouth and preparation of an implantation site therein for replacement of the extracted tooth with a customized restorative prosthesis, are generally known. The construction and implantation of such a restorative prosthesis, including (a) insertion of a metallic fixture into the edentulous bone and (b) the mounting of an abutment support thereon for profiling contact with the gingival gum tissue within the implantation site, is disclosed for example in the Ingber et al. patent aforementioned.

Various problems often arise in connection with the foregoing type of dental implant procedure because of tissue-healing disturbances, customized prosthesis construction difficulties, and tissue profiling to obtain a proper seating fit for the prosthesis within the surgically established implantation site. For example, in prior art, after a fixture has been inserted into edentulous bone in a first stage surgery it is left in place for the necessary healing time required to allow tissue to heal and grow over the implant site, whereupon an incision is made in a second stage surgery and a healing abutment mounted on an exposed protruding hexagonal portion of the fixture. In the prior art, in order to register the implanted fixture position for the purpose of making an impression, it is necessary to remove the healing abutment. This causes tissue healing disturbances. Also, when it is desirable to provide customized prosthesis construction of the type described in the above mentioned patent it is impossible to read information from the positioning of the healing abutment as was done in the prior art which employs standardized permanent abutments. It is therefore an important object of the present invention to avoid or minimize the foregoing problems as well as to reduce restorative rehabilitation time associated with the dental implant procedure.

SUMMARY OF THE INVENTION

In accordance with the present invention, a size selected healing abutment is embedded within surgically exposed edentulous bone and has its one end mounted on the protruding hexagonal end of the fixture. The opposite end of the healing abutment is provided with a registration index. The healing abutment is maintained within the thus formed implantation site in contouring contact with the gingival tissue. An impression coping having a corresponding, mating registration index is then installed on the healing abutment to register its implanted position and indirectly, also at the same time, the implanted position of the fixture. This is accomplished by data transfer of this implanted position to an impression cast replica of the implantation site without removal of the healing abutment therefrom. First, to transfer such data, an impression is made of the actual implantation site with the healing abutment and the impression coping attached thereto. Then, a single-piece analog of the impression coping assembled on the healing abutment and with an implant analog attached thereto, are placed in the impression made of the implantation site to register the implanted position of the healing abutment and the implanted fixture. Then, a stone cast of the implant analog position and of the healing abutment profile in its implanted position is made to form and profile a stone cast replica of the actual implantation site. In this way, position of the implanted fixture in the patient's mouth is registered without any need for removing the healing abutment. After the analog assembly of the healing abutment and impression coping are removed from the stone cast replica, the restorative tooth prosthesis is custom formed on the profiled replica of the implantation site. The healing abutment is finally removed and replaced with the restorative prosthesis after healing of the contoured gingival tissues are complete.

BRIEF DESCRIPTION OF THE DRAWINGS

The nature of the present invention will be more readily understood by reference to the accompanying drawing, in which:

FIG. 6 is a side section view of an impression cast replica of the implantation site, shown in FIGS. 1 and 2, with the analogs of FIG. 5 installed therein;

FIG. 7 is a side section view similar to that of FIG. 6 after the healing abutment-impression coping analog has been removed;

FIG. 8 is a side section view similar to that of FIGS. 6 and 7 with the healing abutment-impression coping analog removed and replaced by assembled portions of the restorative tooth prosthesis;

DETAILED DESCRIPTION OF PREFERRED EMBODIMENTS

Figure 1:
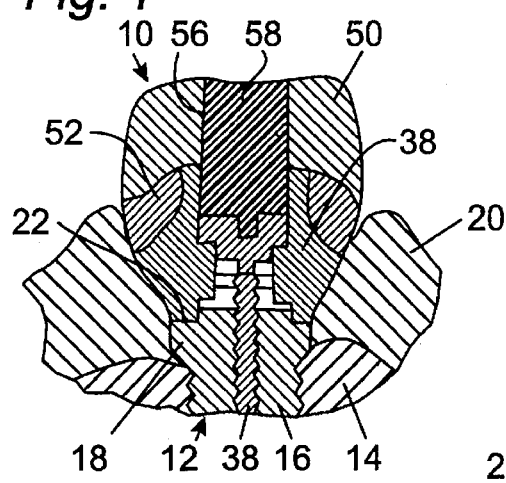
FIG. 1 is a section view of a dental implant installation in accordance with an embodiment of the invention.

Referring now to the drawing in detail, FIG. 1 illustrates a completed restorative tooth prosthesis generally referred to by reference numeral 10. Such prosthesis 10 replaces a single or multiple lost or extracted tooth (teeth), and includes a metallic implant base fixture 12 having an externally threaded body 16 embedded in edentulous bone 14 as disclosed in U.S. Pat. No. 5,125,839 to Ingber et al. aforementioned. The axial end portion 18 of the fixture body 16 extends radially into contact with soft gum tissue 20 within an opening surgically formed therein. The restorative tooth prosthesis 10 is inserted during implantation into such opening. Also, the end portion 18 of the fixture body 16 forms a shoulder surface 22 on which an abutment post 28 of the prosthesis is seated supporting the restoration tooth 50 bonded thereto, for example, by a coping portion 52. The abutment post 28 is held fixed to the bone embedded fixture 12 by a screw fastener 38 installed through an axial access bore 56 in the restoration tooth 50 which is later filled with a resin 58.

Figure 2:
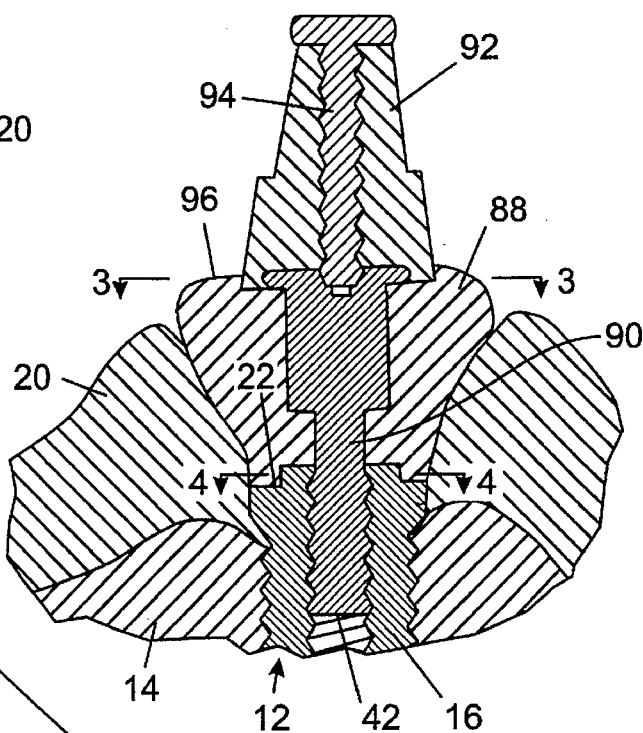
FIG. 2 is a section view similar to that of FIG. 1 showing a healing abutment and impression coping installed in the same implantation site prior to installation of the restorative tooth prosthesis.
Figure 4:
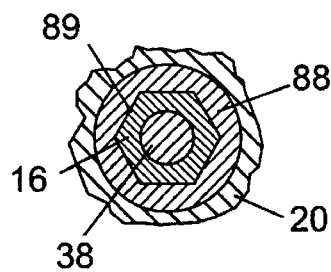
FIG. 4 is a transverse section view taken substantially through a plane indicated by section line 4—4 in FIG. 2.

The implant base fixture 12 is implanted within the edentulous bone 14 after removal therefrom of a fractured tooth or any other faulty tooth unsuitable for conventional therapy. Upon removal of such tooth, a generally known surgical procedure is utilized to initially establish the implantation site by removal of gingival gum tissue to expose the location in the edentulous bone 14 at which the implant base fixture 12 is installed. In accordance with the present invention, a healing abutment 88 of a suitable standard size is selected, as shown in FIG. 2, and is placed on the installed base fixture 12. A central internally shouldered bore in the healing abutment 88 receives a screw fastener 90 by means of which the healing abutment is held seated on the shoulder 22 of the implanted base fixture body 16. The first, seated end of the healing abutment is furthermore formed with a hexagonal recess 89, as'shown in FIG. 4, and is positioned on the protruding hexagonal end of the fixture in a non-rotative fitted relation to the axial end portion of the implanted fixture body 16. Thus, an externally threaded portion of the fastener screw 90 extending from the healing abutment as shown in FIG. 2, is threadedly received in the threaded bore 42 of the base fixture body 16 to thereby hold the healing abutment in place in the implanation site until final delivery of the abutment post 28 with the other portions of the restorative tooth prosthesis 10 assembled thereon. The soft gingival tissue 20 may thereby mature without disturbance for a desired period of time.

Figure 3:
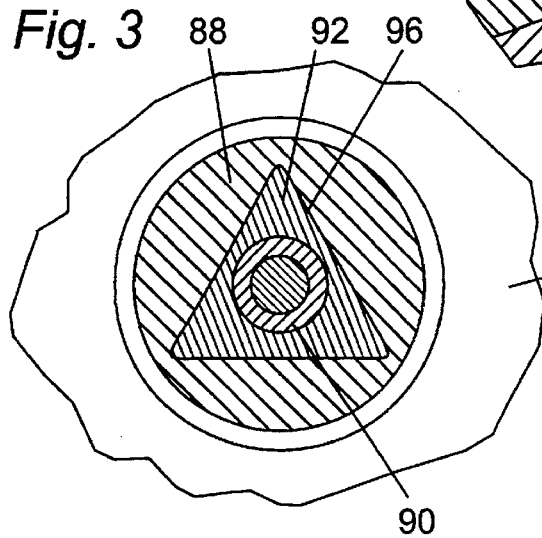
FIG. 3 is a transverse section view taken substantially through a plane indicated by section line 3—3 in FIG. 2.

The second end of the healing abutment 88 is provided with a registration index which, in this preferred embodiment, is formed as a triangular recess 96. However, the registration index can be a recess having any other suitable geometrical form, or a protrusion of suitable geometrical form, etc. After the healing abutment 88 is installed in the implantation site as shown in FIG. 2, a generally conical impression coping 92 of a cross-sectionally triangular shape is seated at its larger end within the triangular recess 96 in the exposed end portion of the healing abutment. The impression coping 92 can have other mating shapes corresponding to the shape of the registration index of the healing abutment. The end portion of fastener screw 90, exposed in the recess 96 of the healing abutment, is thereby covered. A retainer screw 94 threadedly inserted through a bore in the impression coping 92 is received in a threaded opening in the end of the screw 90 to hold the impression Coping affixed to the healing abutment as shown in FIGS. 2 & 3. The purpose for the foregoing placement and fixation of the impression coping 92 on the healing abutment is to register its exact implanted position and, thus, indirectly the position of the implanted fixture so that the dentist can make an impression of the implanted healing abutment with the impression coping 92 assembled thereon.

Figure 5:
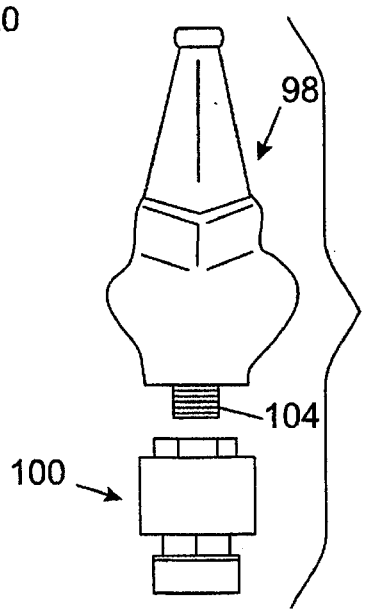
FIG. 5 is a side elevation view of disassembled implant analog of the bone embedded fixture and the one-piece healing abutment-impression coping analog.

In accordance with one embodiment of the invention, the healing abutment 88 is selected from several different standard sizes designed to manage and control the soft gum tissue 20 during the period that it temporarily occupies it's position in the implantation site. The abutment post 28 of the restorative tooth prosthesis 10, is subsequently delivered and installed after removal of the healing abutment 88 from the implantation site. The impression coping 92 mounted on the implanted healing abutment forms an assembly therewith from which an impression is made without removal of the healing abutment from the implantation site. A single-piece type replicating laboratory analog or model 98 with an analog 100 of the base fixture 12, as shown in FIG. 5, is placed into such made impression. These analogs are then seated in a dental stone (plaster) cast replica 102 of the implantation site as shown in FIG. 6. The laboratory analog or model 98 which is secured by a screw 104 to the fixture analog 100 within the stone (plaster) cast replica 102 of the implantation site provides shaping thereof. The laboratory analog or model 98 is then removed from the implantation site replica 102 as shown in FIG. 7 leaving the fixture analog 100 in its registered position corresponding to that of the implanted base fixture 12 and a profiled space there is provided for construction of the prosthesis 10. Construction of the prosthesis 10 as shown in FIG. 8 is initiated by forming the abutment post 28 based on data derived from the assembled healing abutment 88 and impression coping 92 to profile the replica 102 through its analog 98. The abutment post 28 so formed is then secured to the implant fixture analog 100 within replica 102 by means of a screw 38, having its head exposed within the resin filler opening 56 as shown in FIG. 8. The restorative tooth 50 is then formed and bonded in place to the abutment post 28 by means of the coping portion 52 as aforementioned. After being so constructed, the prosthesis is removed from the replica 102 and delivered to the actual implantation site in the patient's mouth for installation therein with the retaining screw 38, after removal of the healing abutment 88. The prosthesis is then completed by filling the opening 56 with the resin 58.

Figure 9:
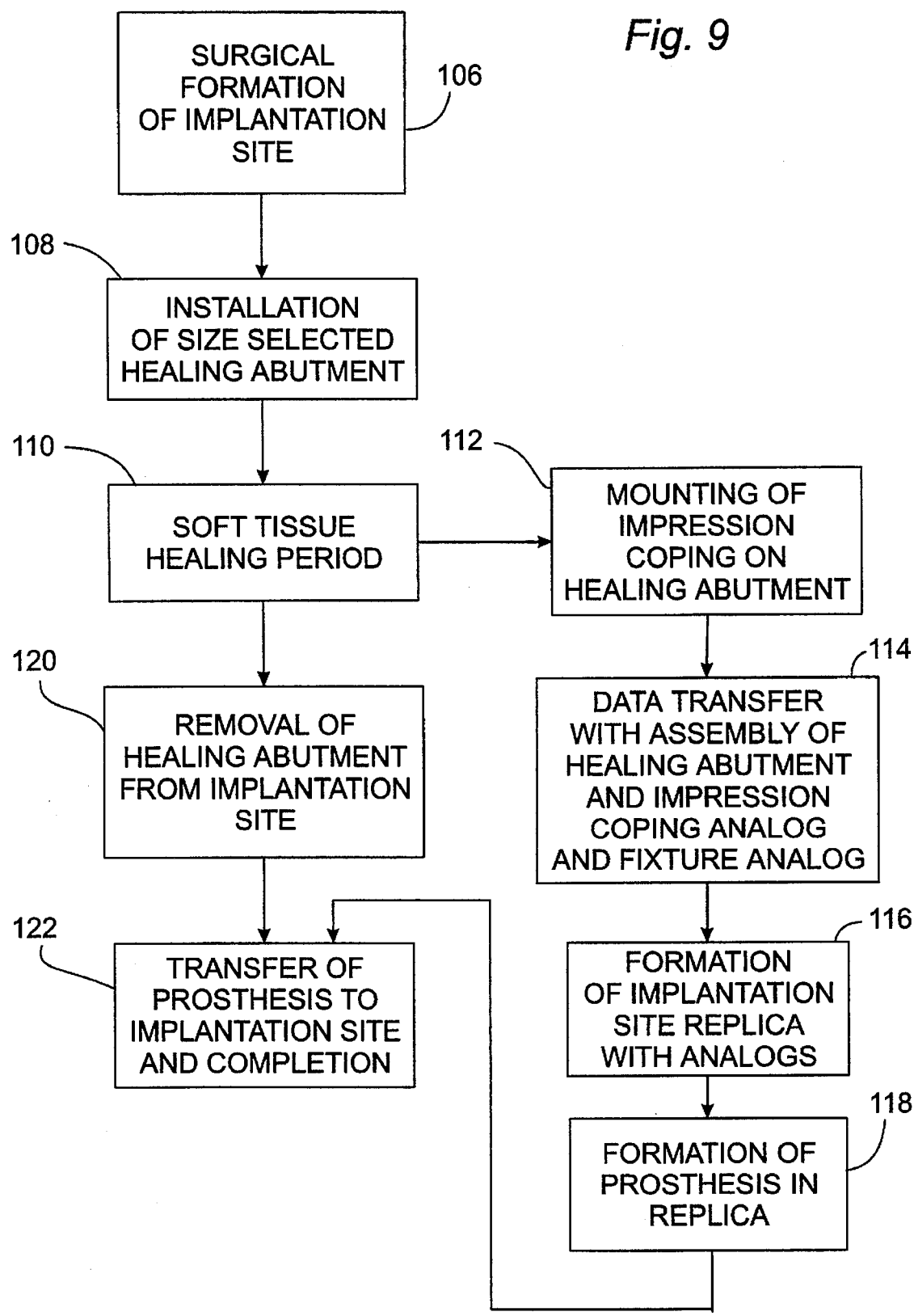
FIG. 9 is a black diagram of the tooth restoration procedure to which FIGS. 1–8 relate.
Figure 10C:
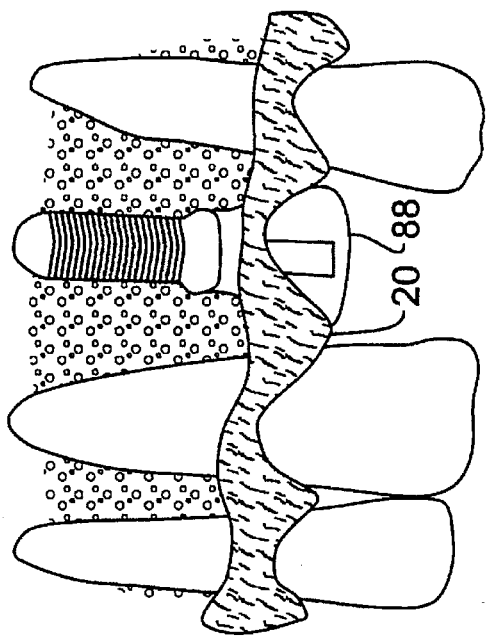
FIGS. 10a–10o illustrate various stages of the tooth restoration according to the present invention method.
Figure 10B:
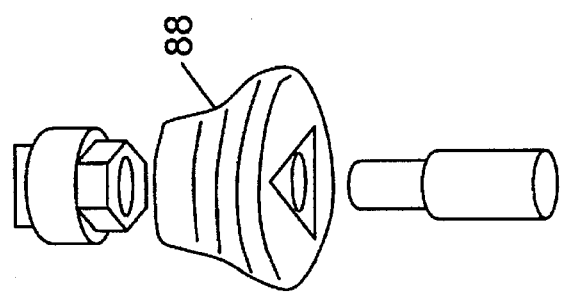
Figure 10A:
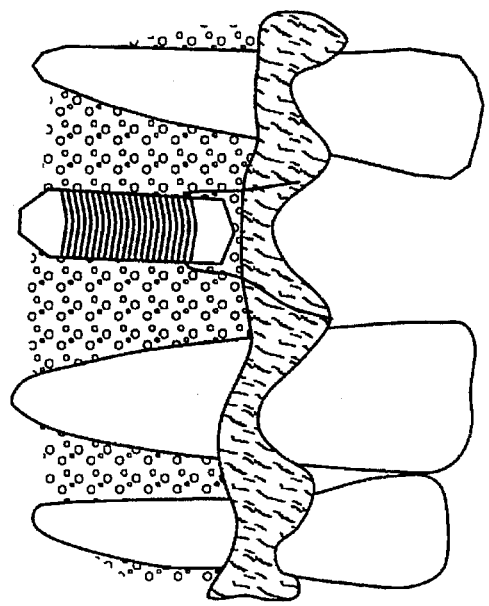
Figure 10F:
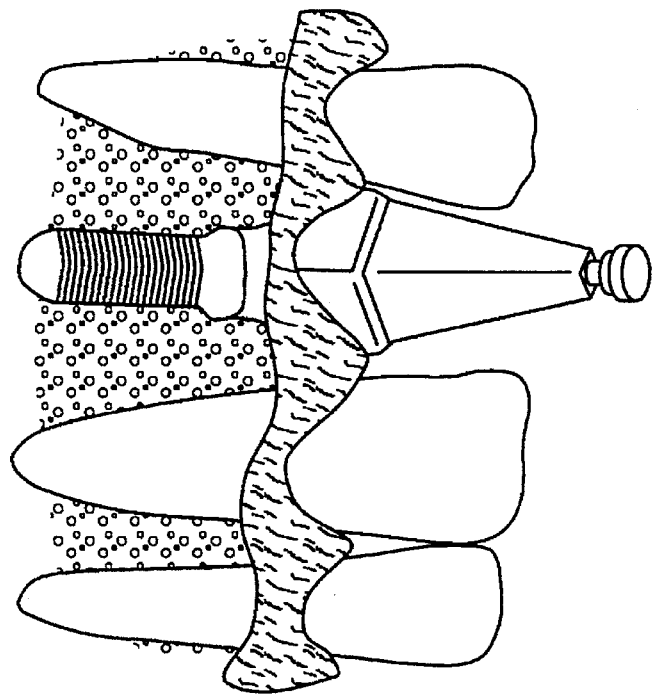
Figure 10E:
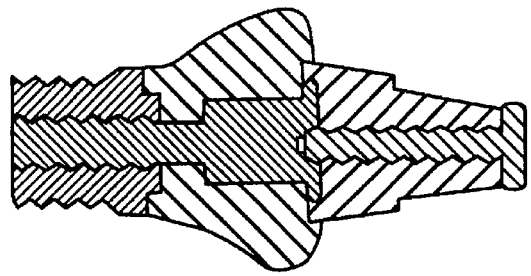
Figure 10D:
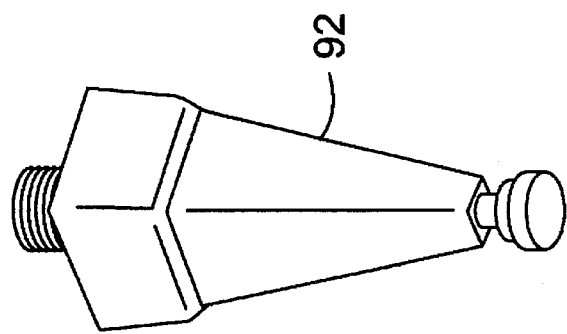
Figure 10H:
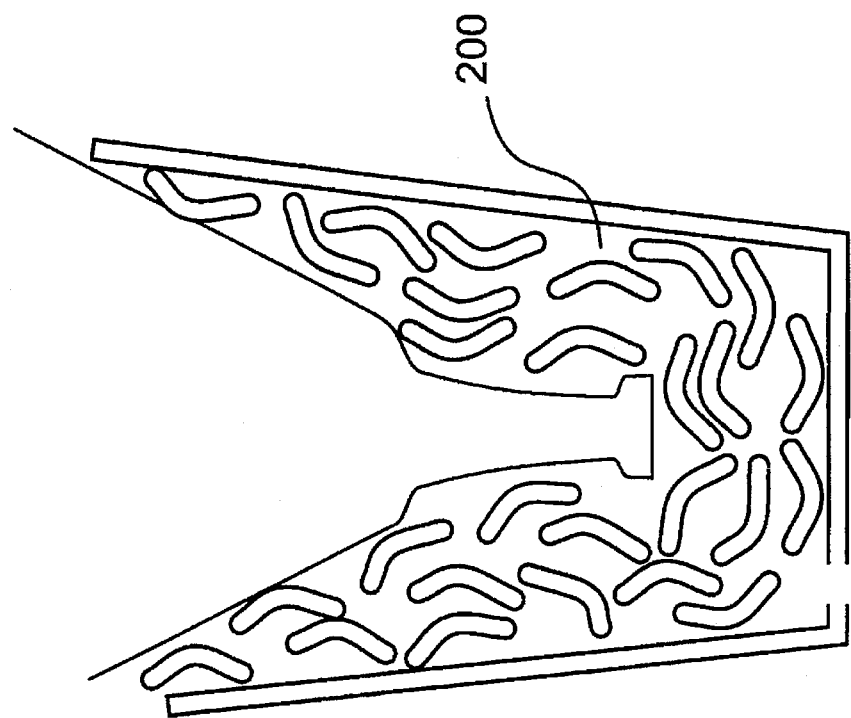
Figure 10G:
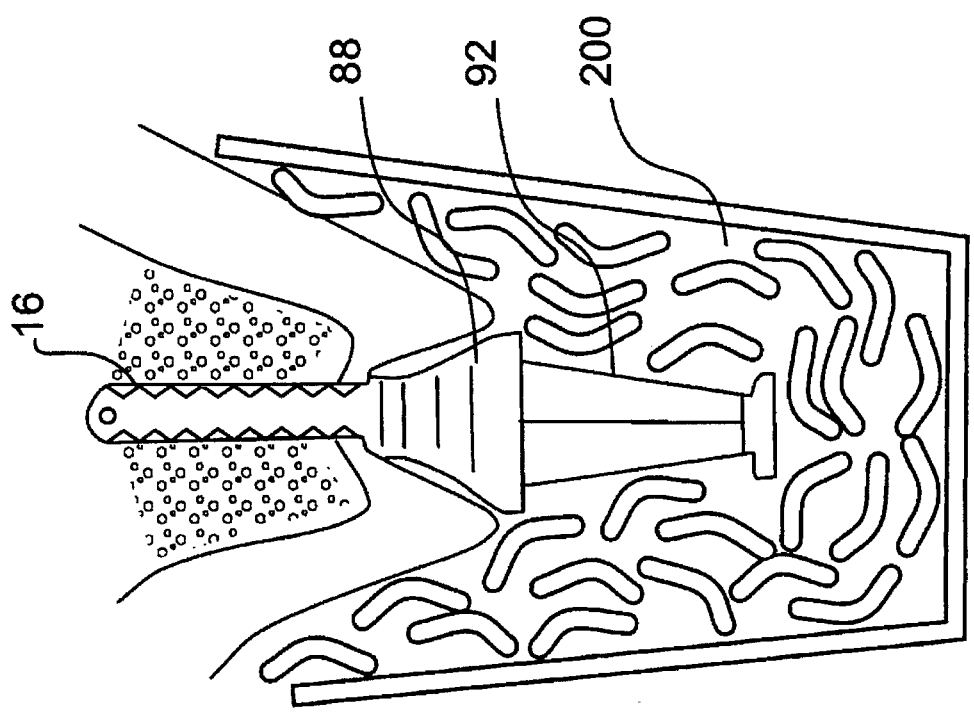
Figure 10J:
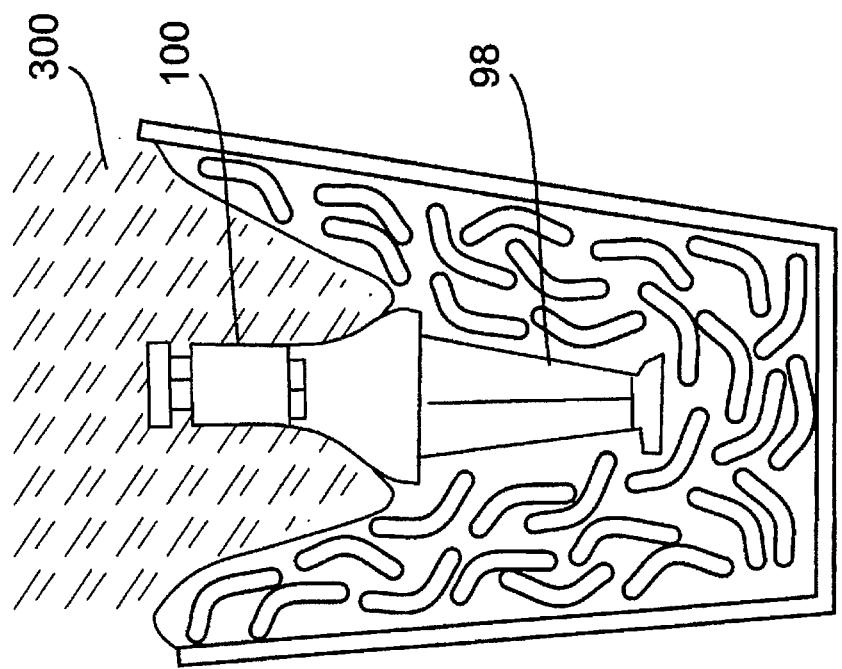
Figure 10I:
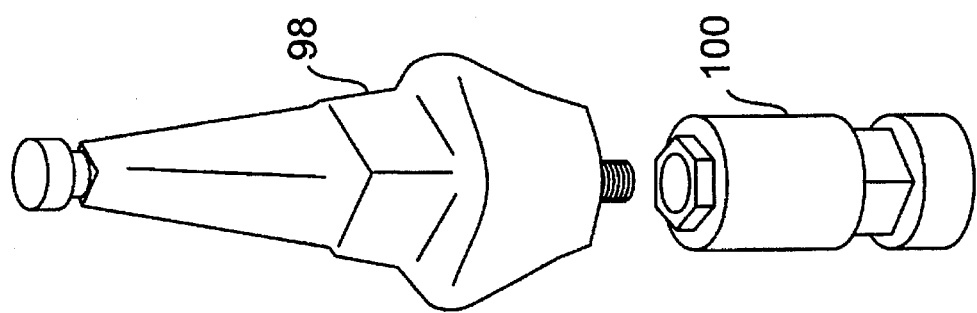

The procedure described above is outlined in the block diagram of FIG. 9 and in FIGS. 10a–o. Initially, the implantation site is surgically formed within a patient's mouth as denoted by block 106 and shown in FIG. 10a. The healing abutment 88 of a selected size and of a type including registration index, as shown in FIG. 10b, is then installed in the implantation site as denoted by block 108 and FIG. 10c. The healing abutment is retained in place for a desired period of time to permit healing of the soft gingival tissue 20 at the implantation site as denoted by block 110. During such healing period, the impression coping 92 having a corresponding complementary registration index as shown in FIG. 10d is mounted on the healing abutment 88 as indicated by block 112 and shown in FIG. 10e and f and an impression 200 is cast of the implantation site as shown in FIG. 10g and 10h. Then, a single-piece healing abutment-impression coping analog 98 is connected to implant analog 100. This assembly, as shown in FIG. 10i, is placed in the impression 200 and a stone cast 300 is made as shown in FIG. 10j and denoted by block 114, for data transfer purposes. Data on the position and shape of the healing abutment, and also data on position of the implanted fixture are thereby utilized to 10 profile the replica 102 of the implantation site as shown in FIG. 10k and as denoted by block 116. After removal of analog 98 from the implantation site replica, a profile space is left as shown in FIG. 10l. The prosthesis 10 is then constructed on the profiled replica 102 in the profiled space as denoted by block 118 and shown in FIG. 10m. Thereafter, the prosthesis 20 (FIG. 10n) is transferred to the actual implantation and completed, as shown by block 122, following removal of the healing abutment from the implantation site, as indicated by block 120, at the end of the healing period as shown in FIG. 10o.

Since the present invention is concerned with installation of a custom made restorative tooth prosthesis which employs a healing abutment for profiling of the implantation site, which is then replaced with a customized permanent abutment, it is important that the data can be read from the implanted fixture position through the registration index of the healing abutment without removal of the healing abutment from the implantation site.

Further it will be appreciated by persons skilled in the art that various deviations from the described embodiments of the invention are possible and that modifications and improvements may be made within the scope of the invention. Thus, it will be understood that the invention is not limited by the specific embodiments, but only by the scope of the appended claims.

We claim:

1. In a dental implant method of installing a restorative tooth prosthesis in an implantation site formed within edentulous bone surgically exposed through gingival tissue and wherein said prosthesis is constructed within a replica of the implantation site, comprising the steps of:

dimensionally selecting a healing abutment to fit into the implantation site;

implanting the selected healing abutment within the implantation site in contact with the gingival tissue for contouring thereof;

transferring data from the implanted healing abutment to the replica of the implantation site prior to formation of the prosthesis therein without removal of the healing abutment from the implantation site; and replacing the implanted healing abutment within the implantation site with the prosthesis after healing of the gingival tissue contoured by the implanted healing abutment.

2. The method as defined in claim 1 wherein said step of transferring data includes affixing an impression coping on the selected healing abutment after said implanting thereof to register implantation position within said implantation site; forming an impression mold of implantation site with the implanted healing abutment and the impression coping affixed thereto.

3. The method as defined in claim 2 wherein said healing abutment and said impression coping are provided with corresponding registration index portions.

4. The method as defined in claim 1 wherein the implantation site is established by embedding in the exposed edentulous bone a base fixture having a bore adapted to sequentially receive fasteners from the selected healing abutment and the prosthesis respectively, during said steps of implanting the healing abutment and replacing thereof with the prosthesis.

5. The method as defined in claim 4 wherein said step of transferring data further includes positioning a healing abutment impression coping analog with a fixture analog connected thereto in said impression mold.

6. The method as defined in claim 4 wherein said step of transferring data further includes making a stone cast over said implant analog and said healing abutment-impression coping analog as positioned in said impression mold for providing the replica of the implantation site.

7. The method as defined in claim 1 wherein said step of selecting the healing abutment comprises selection from a plurality of different standard size abutments.

8. The method as defined in claim 1 wherein the implantation site is established by embedding in the exposed edentulous bone a base fixture having a bore adapted to sequentially receive fasteners from the selected healing abutment and the prosthesis respectively, during said steps of implanting the healing abutment and replacing thereof with the prosthesis.

* * * * *